United States Patent
Kuo (10) Patent No.: US 8,275,180 B2
(45) Date of Patent: Sep. 25, 2012

(54) MAPPING ABNORMAL DENTAL REFERENCES

(75) Inventor: Eric E. Kuo, Foster City, CA (US)

(73) Assignee: Align Technology, Inc., San Jose, CA (US)

( * ) Notice: Subject to any disclaimer, the term of this patent is extended or adjusted under 35 U.S.C. 154(b) by 1079 days.

(21) Appl. No.: 11/888,742

(22) Filed: Aug. 2, 2007

(65) Prior Publication Data

US 2009/0034811 A1   Feb. 5, 2009

(51) Int. Cl.
*G06K 9/00* (2006.01)
*G06K 9/46* (2006.01)
*A61C 3/00* (2006.01)
*A61B 1/00* (2006.01)

(52) U.S. Cl. ........ 382/128; 382/209; 382/284; 382/288; 433/68; 433/167; 433/213

(58) Field of Classification Search .................. 382/128, 382/209, 284, 288; 433/68, 167, 213
See application file for complete search history.

(56) References Cited

U.S. PATENT DOCUMENTS

| | | | |
|---|---|---|---|
| 5,879,158 A * | 3/1999 | Doyle et al. .................. 433/24 |
| 5,882,192 A | 3/1999 | Bergersen |
| 6,394,802 B1 | 5/2002 | Hahn |
| 6,632,089 B2 | 10/2003 | Rubbert et al. |
| 6,648,640 B2 * | 11/2003 | Rubbert et al. ............... 433/24 |
| 6,733,289 B2 * | 5/2004 | Manemann et al. .......... 433/24 |
| 6,772,026 B2 | 8/2004 | Bradbury et al. |
| 6,832,914 B1 | 12/2004 | Bonnet et al. |
| 7,245,753 B2 * | 7/2007 | Squilla et al. ................ 382/128 |
| 7,471,821 B2 * | 12/2008 | Rubbert et al. ............... 382/154 |
| 7,740,476 B2 | 6/2010 | Rubbert et al. |
| 7,826,646 B2 * | 11/2010 | Pavlovskaia et al. ......... 382/128 |
| 2002/0015934 A1 | 2/2002 | Rubbert et al. |
| 2003/0021453 A1 * | 1/2003 | Weise et al. .................. 382/128 |
| 2004/0029078 A1 * | 2/2004 | Marshall .................... 433/217.1 |
| 2004/0265770 A1 * | 12/2004 | Chapoulaud et al. .......... 433/24 |
| 2005/0233276 A1 * | 10/2005 | Kopelman et al. .............. 433/3 |
| 2005/0239013 A1 * | 10/2005 | Sachdeva ....................... 433/24 |
| 2006/0063135 A1 * | 3/2006 | Mehl ............................ 433/223 |
| 2006/0204078 A1 | 9/2006 | Orth et al. |
| 2007/0172291 A1 | 7/2007 | Yokoyama |
| 2008/0090208 A1 | 4/2008 | Rubbert |

FOREIGN PATENT DOCUMENTS

WO   WO 03/099155 A1   12/2003
WO   WO 03/101330 A2   12/2003

OTHER PUBLICATIONS

International Search Report for related PCT Application PCT/US2008/009328 dated Nov. 6, 2008. (5 pgs.)
Wong, Ricky Wing-Kit, et al. "The uses of orthodontic study models in diagnosis and treatment planning". Hong Kong Dental Journal, 2006;3:107-115.

* cited by examiner

*Primary Examiner* — Michael A Newman
(74) *Attorney, Agent, or Firm* — Brooks, Cameron & Huebsch, PLLC (57) ABSTRACT

Embodiments are provided for accurately characterizing a tooth's movement. One method embodiment includes associating an abnormal tooth shape with a model tooth shape from a reference library of model tooth shapes, mapping a predefined dental reference from the model tooth shape onto at least a portion of the abnormal tooth shape, and adding a location of the predefined dental reference to the abnormal tooth shape based on the mapped predefined dental reference from the model tooth shape.

21 Claims, 8 Drawing Sheets

MAPPING ABNORMAL DENTAL REFERENCES

BACKGROUND

The present disclosure is related generally to the field of orthodontics. More particularly, the present disclosure is related to a dental model system which can associate an abnormal tooth with a model tooth shape and map predefined dental references from the model shape onto the abnormal tooth to aid in accurately characterizing the tooth's positioning and/or movement.

Dental references provide feedback for dental measurements. For example, dental reference points can be used to characterize a tooth's movement, such as tipping and/or translation. Dental reference axes can be used to distinguish different directions of tooth positioning and/or movement.

Placement and/or identification of reference points can be done manually by a treatment professional or automatically through use of a computing device and executable instructions to make such identification and/or direct one or more devices to accomplish such placement. For example, the treatment professional can use a computing interface device to identify points on an image of a tooth displayed on a graphical user interface.

The treatment professional can also identify reference axes of the tooth in a similar fashion. However, manual selection of reference points and axes can yield inaccurate and inconsistent results.

As discussed above, automation of reference point selection can be performed with the assistance of a computing device. Algorithms in computing device-aided recognition of surface features can improve accuracy in some instances. For example, the maximum height of a crown can be detected by an algorithm that determines the location of cusp tips and this may improve the accuracy of reference point selection.

However, such automated systems are based on the assumption that the dental anatomy is normal. That is, the assumption that a tooth is fully intact and fully erupted.

Such automated systems rely on a set of dental features to identify reference points and axes. If a tooth is broken or partially erupted, an automated system may rely on incorrect landmarks to derive the reference points and axes.

In such situations, the automated system can incorrectly identify reference points and axes. This may result in impractical or incorrect treatment options.

DETAILED DESCRIPTION

Embodiments of the present disclosure include computing device, system, and method embodiments for mapping abnormal dental references. For example, the embodiments include, a computing device readable medium having instructions for associating an abnormal tooth shape with a model tooth shape from a reference library of model tooth shapes. This can be beneficial, for example, in aiding the treatment professional with visualization of references for an abnormal tooth, among other benefits.

References can include those which might not be visible on an abnormal tooth due to its abnormality. For example, a chipped tooth could be missing a portion of the tooth where a dental reference is located. Associating an abnormal tooth with a model tooth shape can aid the treatment professional in visualizing missing references.

Some embodiments can include mapping a predefined dental reference from the model tooth shape onto at least a portion of the abnormal tooth shape. This can be beneficial in providing the treatment professional with more accurate and consistent references over manual selection of references based on the treatment professional's estimation, among other benefits.

Figure 1A:
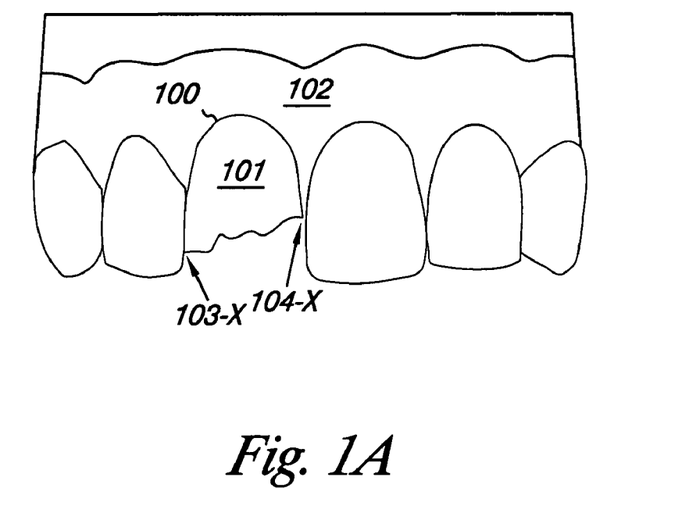
FIG. 1A illustrates an example of a broken tooth.

Referring now to the embodiment illustrated in FIG. 1A, FIG. 1A illustrates an abnormal tooth 100 that is broken, such that a piece of the dental crown is missing. An automated system, known and used by one of ordinary skill in the art, operating on the assumption that the tooth 100 is normal, would interpret 103-X as one cusp tip while interpreting 104-X as another. FIG. 1A also displays the cementoenamel junction (CEJ) 101 and gingiva 102.

Figure 1B:
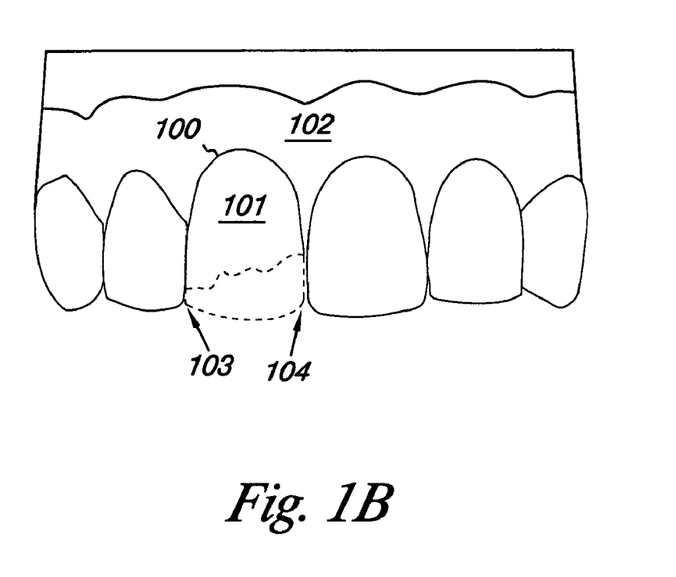
FIG. 1B illustrates the broken tooth of FIG. 1A and includes an outline of the model shape of the tooth.

FIG. 1B illustrates the broken tooth of FIG. 1A and includes an outline of what the model shape of the tooth, 100 would be, if it had not been damaged. The actual locations of the cusp tips 103 and 104 are shown.

In various embodiments, an embodiment can include adding a location of the predefined dental reference to the abnormal tooth shape based on the mapped predefined dental reference from the model tooth shape. This can aid the treatment professional when correction of the abnormal tooth involves treatment in consideration of that reference point.

Embodiments can include executable instructions for mapping the predefined dental reference from the model tooth onto at least a portion of the abnormal tooth by superimposing the model tooth shape on the abnormal tooth shape. This can be beneficial in matching the model tooth shape with the actual tooth by aligning reference points.

In some embodiments, instructions can be included to create a dental image that contains at least a portion of the abnormal tooth shape and at least a portion of the model tooth shape. Such embodiments can be beneficial, for example, to aid the treatment professional in visualizing the abnormal tooth as a normal tooth.

In some embodiments, instructions can map a predefined gingival reference from the reference library corresponding to the model tooth shape onto a gingival anatomy of the abnormal tooth shape, where the dental image contains at least a portion of the abnormal tooth shape gingival anatomy and at least a portion of the model tooth shape gingival anatomy. This can be beneficial in allowing the treatment professional to visualize and accommodate changes to the gingival architecture that may occur as teeth move and erupt in accordance with orthodontic treatment and/or tooth maturation.

In some embodiments, instructions can be included for mapping the predefined dental reference from the model tooth shape onto at least a portion of the abnormal tooth shape and can include virtually mapping a portion of the predefined dental reference that does not correspond to a location on the abnormal tooth shape. Such embodiments can be beneficial, for example, in allowing the treatment professional to visualize the correct reference points and axes in order to properly characterize a tooth's movement.

In some embodiments, instructions can be executed to determine a center of rotation of the abnormal tooth shape using the location of the predefined dental references on the abnormal tooth shape based on the mapped predefined dental references from the model tooth shape.

Embodiments of the present disclosure are able to accurately identify the model locations of these reference points, for example, based on associating one or more images of model tooth shapes from the reference library with these abnormal teeth and mapping predefined dental references from the model shapes onto the abnormal tooth shapes. The locations of the CEJ 101 and gingiva 102 remain the same as in FIG. 1A.

Figure 1C:
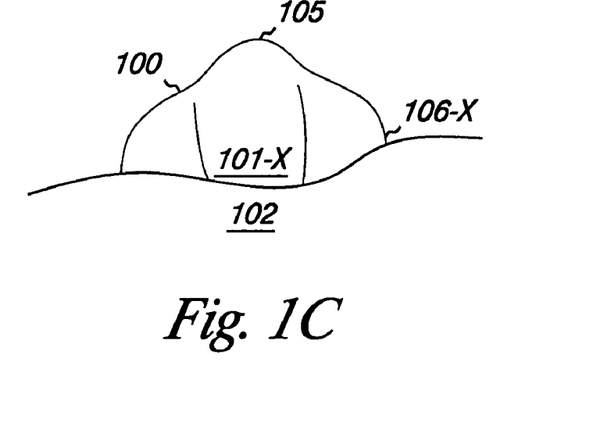
FIG. 1C illustrates an example of a partially erupted tooth.

FIG. 1C illustrates an abnormal tooth 100 that is partially erupted. This tooth includes a cusp tip 105 and gingiva 102. An automated system operating on the assumption that the tooth is normal, could incorrectly interpret 106-X as a proximal contact and 101-X as the CEJ.

Figure 1D:
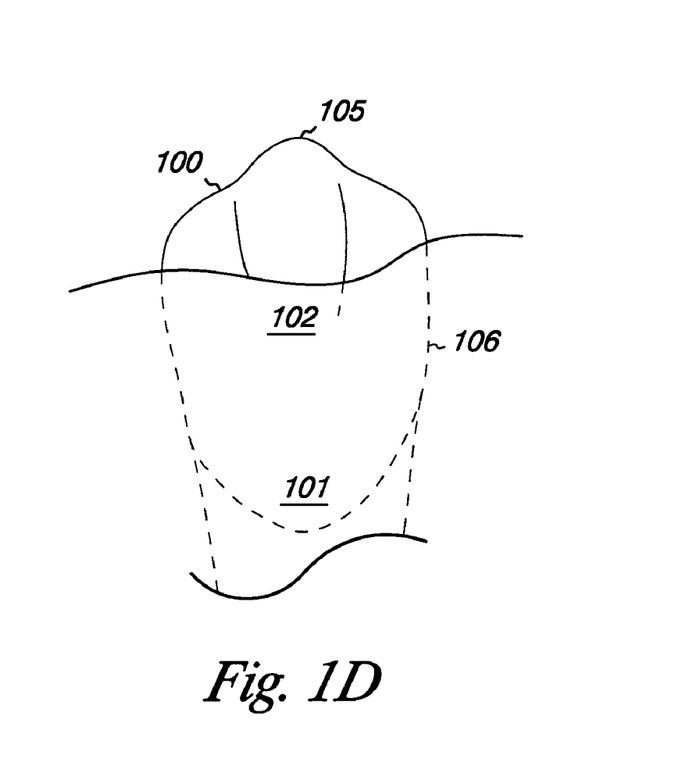
FIG. 1D illustrates the partially erupted tooth of FIG. 1C and includes an outline of a model shape of the unerupted portion of the tooth.

FIG. 1D illustrates the partially erupted tooth 100 of FIG. 1C. This tooth includes a cusp tip 105 and gingiva 102. This Figure indicates the approximate location of the proximal contact 106 and CEJ 101. Embodiments of the present disclosure can be utilized to accurately identify the model locations of these reference points, for example, based on associating one or more images of model tooth shapes from the reference library with these abnormal teeth and mapping predefined dental references from the model shapes onto the abnormal tooth shapes.

Figure 2:
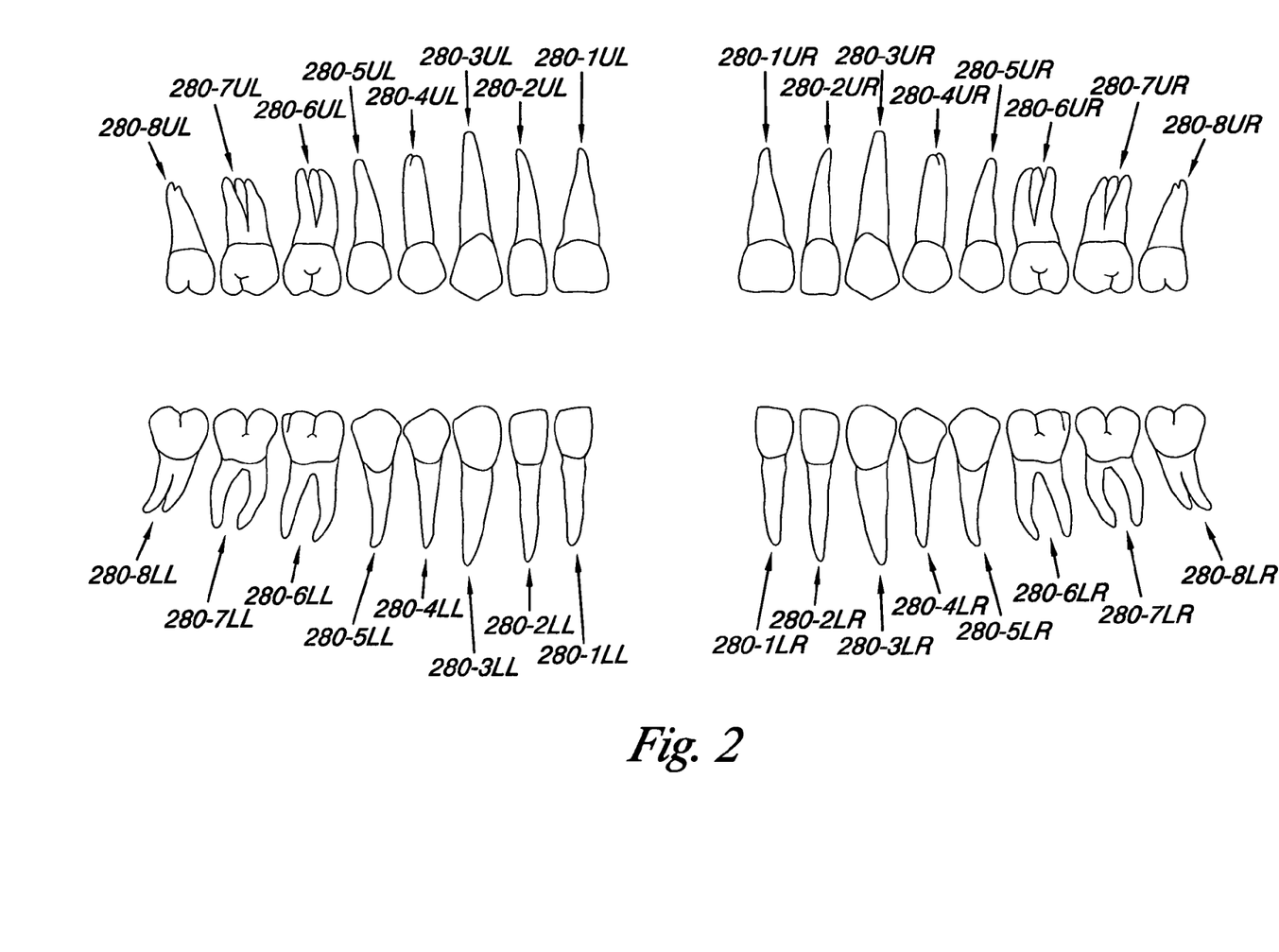
FIG. 2 illustrates a reference library of model tooth shapes.

FIG. 2 illustrates a reference library of model tooth shapes. FIG. 2 includes reference teeth for the upper right (280-1UR, 280-2UR, 280-3UR, 280-4UR, 280-5UR, 280-6UR, 280-7UR, and 280-8UR), upper left (280-1UL, 280-2UL, 280-3UL, 280-4UL, 280-5UL, 280-6UL, 280-7UL, and 280-8UL), lower right (280-1LR, 280-2LR, 280-3LR, 280-4LR, 280-5LR, 280-6LR, 280-7LR, and 280-8LR), and lower left (280-1LL, 280-2LL, 280-3LL, 280-4LL, 280-5LL, 280-6LL, 280-7LL, and 280-8LL) groupings of teeth.

The reference library of model tooth shapes can also contain several reference points and axes for one or more teeth in the library. For instance, an example of a tooth with a plurality of reference points is illustrated in FIGS. 3A and 3B.

For instance, a theoretical root axis of a tooth may be important to accurately determine in a broken tooth, for example, if trying to assess an ideal orientation for the placement of a replacement tooth root device, such as a dental implant, using the existing broken tooth as a guide. The root axis may be more accurately determined using a superimposed ideal tooth model as opposed to using the existing broken tooth geometry as a basis for axis position determination, in some instances.

Figure 3A:
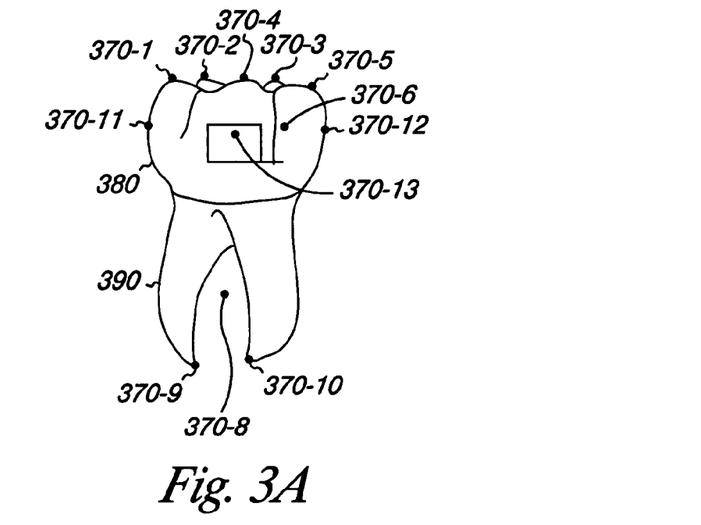
FIG. 3A illustrates a buccal view of a lower right molar selected from the reference library of model tooth shapes according to embodiments of the present disclosure.
Figure 3B:
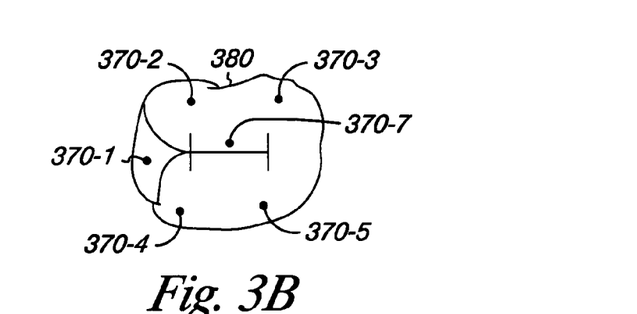
FIG. 3B illustrates an occlusal view of a lower right molar selected from the reference library of model tooth shapes according to embodiments of the present disclosure.

FIG. 3A illustrates a buccal view of a model tooth shape 380 from the reference library in FIG. 2. The tooth shape 380 illustrated in FIG. 3A is a lower right molar, for example, 280-6LR from FIG. 2. FIG. 3A also indicates the root shape 390 of the tooth shape 380.

The tooth shape in FIG. 3A is labeled with, for example, reference points (370-1, 370-2, 370-3, 370-4, 370-5, 370-6, 370-8, 370-9, 370-10, 370-11, 370-12, and 370-13) stored in the reference library. For instance, reference point 370-1 illustrates a point on the distal cusp tip.

Reference point 370-2, similarly is used to illustrate a point, on the distal lingual cusp tip, on the tooth. Reference point 370-3 illustrates a point on the mesial lingual cusp tip.

FIG. 3A, also includes reference point 370-4 that illustrates a point on the distal buccal cusp tip. Also, reference point 370-5 illustrates a point on the mesial buccal cusp tip.

Reference line 370-6 illustrates the facial aspect of clinical crown (FACC) line. Reference point 370-8 illustrates the center of resistance. Reference point 370-9 illustrates a point on the distal root tip. Reference point 370-10 illustrates a point on the mesial root tip.

Reference point 370-11 illustrates the distal contact point. Reference point 370-12 illustrates the mesial contact point. Reference point 370-13 illustrates a correct position for a virtual bracket or other dental appliance.

FIG. 3B illustrates an occlusal view of the model tooth shape 380 from the reference library in FIG. 2. The tooth shape in FIG. 3B is labeled with, for example, reference points (370-1, 370-2, 370-3, 370-4, 370-5, and 370-7).

For instance, reference point 370-1 illustrates a point on the distal cusp tip. Reference point 370-2 illustrates a point on the distal lingual cusp tip.

FIG. 3B also includes reference point 370-3 that illustrates a point on the mesial lingual cusp tip. Reference point 370-4 illustrates a point on the distal buccal cusp tip of the tooth.

Reference point 370-5 illustrates a point on the mesial buccal cusp tip. Reference line 370-7 illustrates the central groove.

Figure 3C:
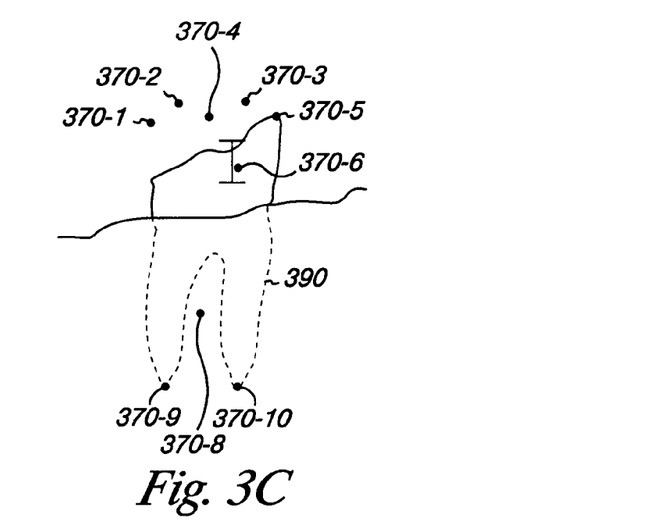
FIG. 3C illustrates reference points from a model tooth shape applied to a broken tooth according to embodiments of the present disclosure.

FIG. 3C illustrates an abnormal tooth that is broken. The tooth in FIG. 3C is a lower right molar as in FIGS. 3A and 3B. The location of the root 390 is outlined in FIG. 3C. Reference points (370-1, 370-2, 370-3, 370-4, 370-5, 370-6, 370-8, 370-9, and 370-10) from the reference library are superimposed on the tooth in the positions they would assume had the tooth not been broken, according to an embodiment of the present disclosure.

Reference point 370-1 illustrates a point on the distal cusp tip. Similarly, the reference point 370-2 illustrates a point on the distal lingual cusp tip of the tooth. Reference point 370-3 illustrates a point on the mesial lingual cusp tip.

Additionally, reference point 370-4 illustrates a point on the distal buccal cusp tip of the tooth. Reference point 370-5 illustrates a point on the mesial buccal cusp tip.

Reference line 370-6 illustrates the facial aspect of clinical crown (FACC) line. Reference point 370-8 illustrates the center of resistance. Reference point 370-9 illustrates a point on the distal root tip. Reference point 370-10 illustrates a point on the mesial root tip.

Figure 4A:
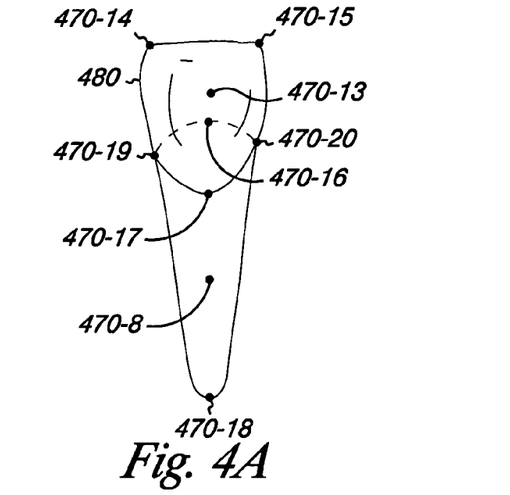
FIG. 4A illustrates a model tooth shape selected from the reference library of model tooth shapes according to embodiments of the present disclosure.

FIG. 4A illustrates a model tooth shape 480 from the reference library of FIG. 2. The tooth shape 480 illustrated in FIG. 4A is a lower incisor, for example, 280-1LR from FIG. 2.

Several reference points are labeled on the tooth. Reference point 470-8 illustrates the center of resistance of the tooth. Reference point 470-13 illustrates a correct position for a virtual bracket.

Reference points 470-14 and 470-15 illustrate points on opposite cusp tips. Reference point 470-18 illustrates a point on the root tip.

Reference points 470-16, 470-17, 470-19, and 470-20 illustrate additional reference points that could be used by one of ordinary skill in the art to accurately characterize a tooth's movement using an embodiment of the present disclosure.

Figure 4B:
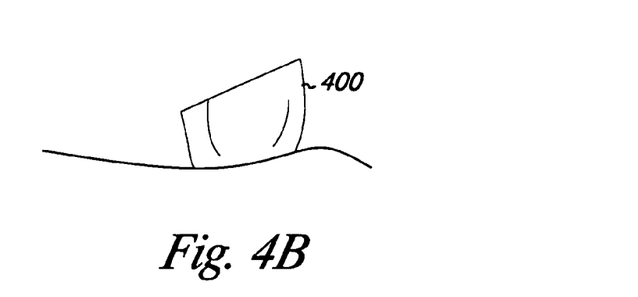
FIG. 4B illustrates an example of a broken tooth.

FIG. 4B illustrates an abnormal tooth that is broken. The tooth 400 in FIG. 4B is a lower incisor as in FIG. 4A.

Figure 4C:
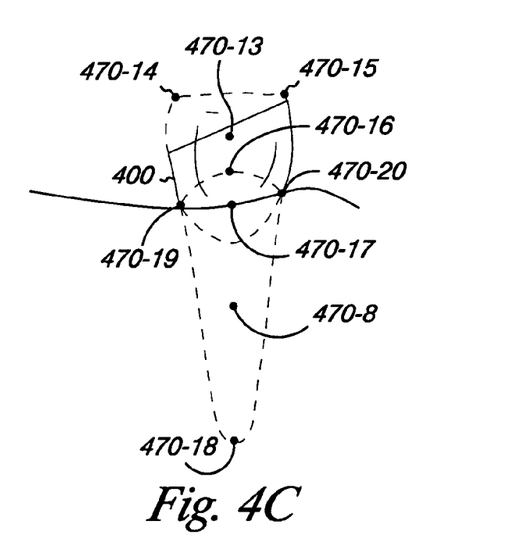
FIG. 4C illustrates reference points from a model tooth shape transferred onto an example of a broken tooth according to embodiments of the present disclosure.

FIG. 4C illustrates the model tooth shape 480 of FIG. 4A superimposed on the abnormal tooth 400 of FIG. 4B according to an embodiment described herein. The reference points described above with respect to FIG. 4A are also transferred onto the abnormal tooth 400.

Reference point 470-8 illustrates the center of resistance of the tooth. Reference point 470-13 illustrates a correct position for a virtual bracket.

Reference points 470-14 and 470-15 illustrate points on opposite cusp tips. Reference point 470-18 illustrates a point on the root tip.

Reference points 470-16, 470-17, 470-19, and 470-20 illustrate additional reference points that could be used by one of ordinary skill in the art to accurately characterize a tooth's movement using an embodiment of the present disclosure.

In some embodiments, the computing device superimposes the model tooth shape on the abnormal tooth shape by a shrink-wrap sizing algorithm. This is illustrated in FIGS. 5A-5C.

Figure 5A:
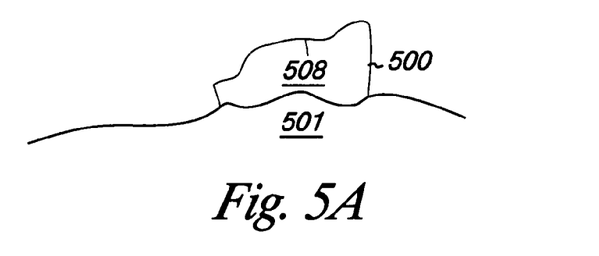
FIG. 5A illustrates an example of a broken tooth.

For example, FIG. 5A illustrates an abnormal tooth that is broken. Tooth 500 is a lower molar. FIG. 5A also illustrates the CEJ at 501. The crown of the tooth 500 is provided at 508.

Figure 5B:
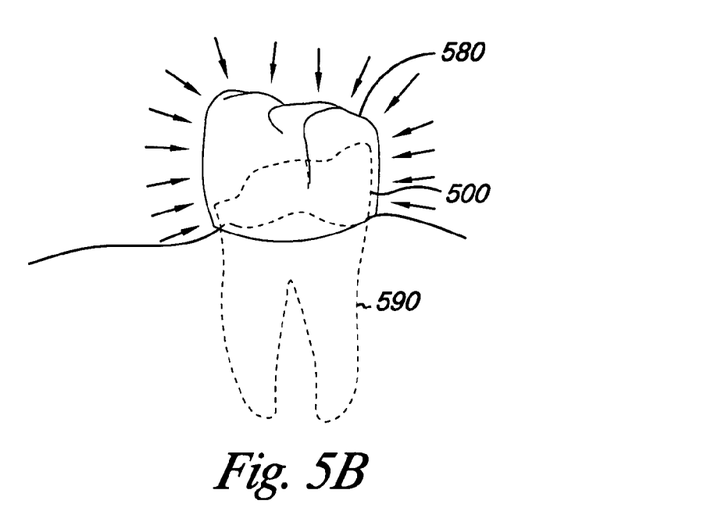
FIG. 5B illustrates the operation of a shrink-wrap algorithm matching a model tooth shape from the reference library to the broken tooth of FIG. 5A according to embodiments of the present disclosure.
Figure 5C:
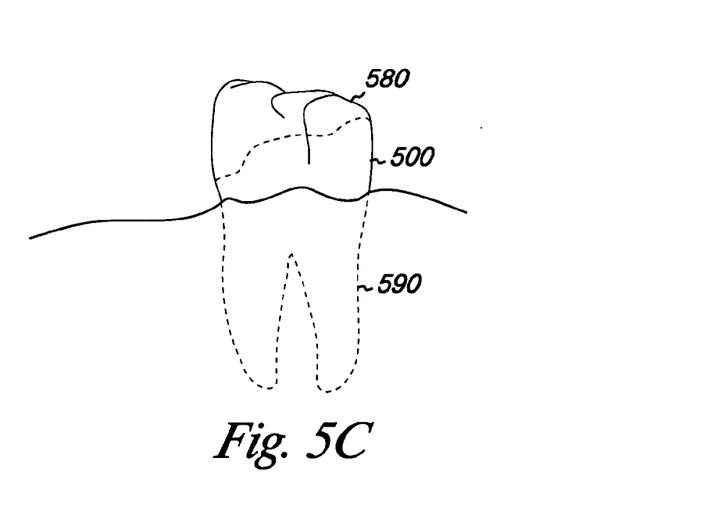
FIG. 5C illustrates the image of the model tooth shape superimposed on the broken tooth after operation of the shrink-wrap algorithm according to embodiments of the present disclosure.

FIG. 5B illustrates a model tooth shape 580 superimposed over the broken tooth 500 from FIG. 5A. The root of the model tooth shape 580 is illustrated at 590.

The arrows indicate that the model tooth shape 580 is being shrink-wrapped according to an embodiment described herein. The shrink-wrap operation can, for example, utilize executable instructions to scale the size of the model tooth shape 580 down so that one or more of its reference points correspond to one or more reference points of the abnormal tooth 500.

FIG. 5C illustrates the model tooth shape 580 from FIG. 5B after it has been reduced by the shrink-wrap operation according to an embodiment described herein. In FIG. 5C, the model tooth shape 580 is collinear with the outer, normal surfaces of the abnormal tooth 500.

The outer, normal surfaces of abnormal tooth 500 are those outer surfaces, which would be continue to be outer surfaces if the abnormal tooth 500 were unbroken and fully erupted. An outline of the root 590 may also be provided to aid in the fit in some embodiments.

In some embodiments, the portion of the tooth to be modeled may be below, at, or transiting the gingiva adjacent to the tooth. In such embodiments, executable instructions can be utilized in the mapping of a predefined dental reference from a model tooth shape onto at least a portion of the abnormal tooth shape where the mapping includes virtually mapping a portion of the predefined dental reference that is at least partially obscured by the gingiva.

Figure 6:
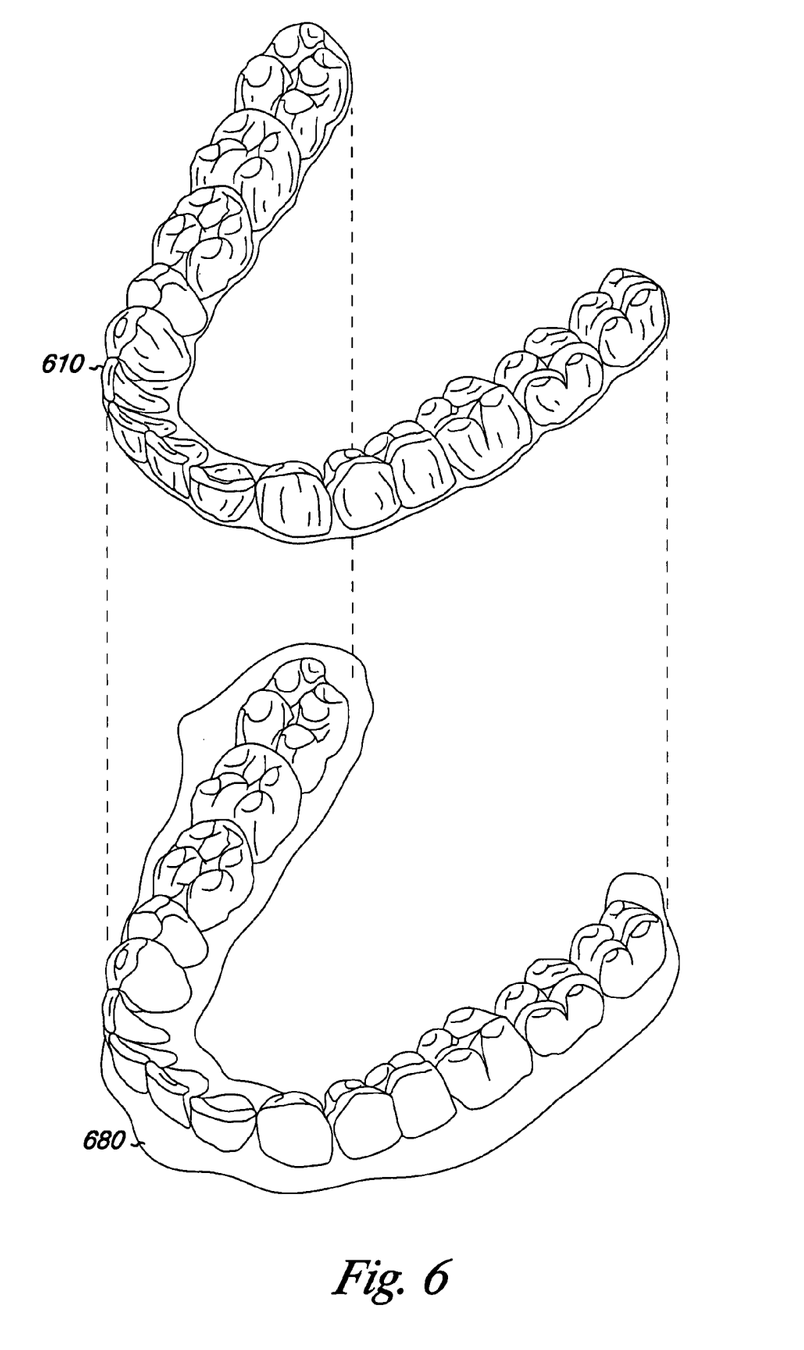
FIG. 6 illustrates an appliance being applied to a set of teeth that has been prepared according to embodiments of the present disclosure.

FIG. 6 illustrates a position adjustment appliance 610 that can be fitted over a set of teeth 680. Appliances according to the present disclosure include a plurality of incremental position adjustment appliances. The appliances, such as appliance 610 illustrated in FIG. 6, can be utilized to affect incremental repositioning of individual teeth in the jaw 680 as described generally above, among other suitable uses.

The methods of the present disclosure can employ any positioners, retainers, and/or other removable appliances for finishing and maintaining teeth positions in connection with a dental treatment. These appliances may be utilized by the dental professional in performing his treatment plan that was created using some of the methods described herein.

In some embodiments, instructions can be executed to create an orthodontic treatment plan based on the location of the predefined dental references on the abnormal tooth shape. Such an embodiment may also include creating a predefined set of appliances for placement over one or more teeth.

An appliance (e.g., appliance 610 in FIG. 6) can, for example, be fabricated from a polymeric shell, or formed from other material, having a cavity shaped to receive and apply force to reposition one or more teeth from one teeth arrangement to a successive teeth arrangement. The shell may be designed to fit over a number of, in many instances all teeth, present in the upper or lower jaw 680.

Figure 7:
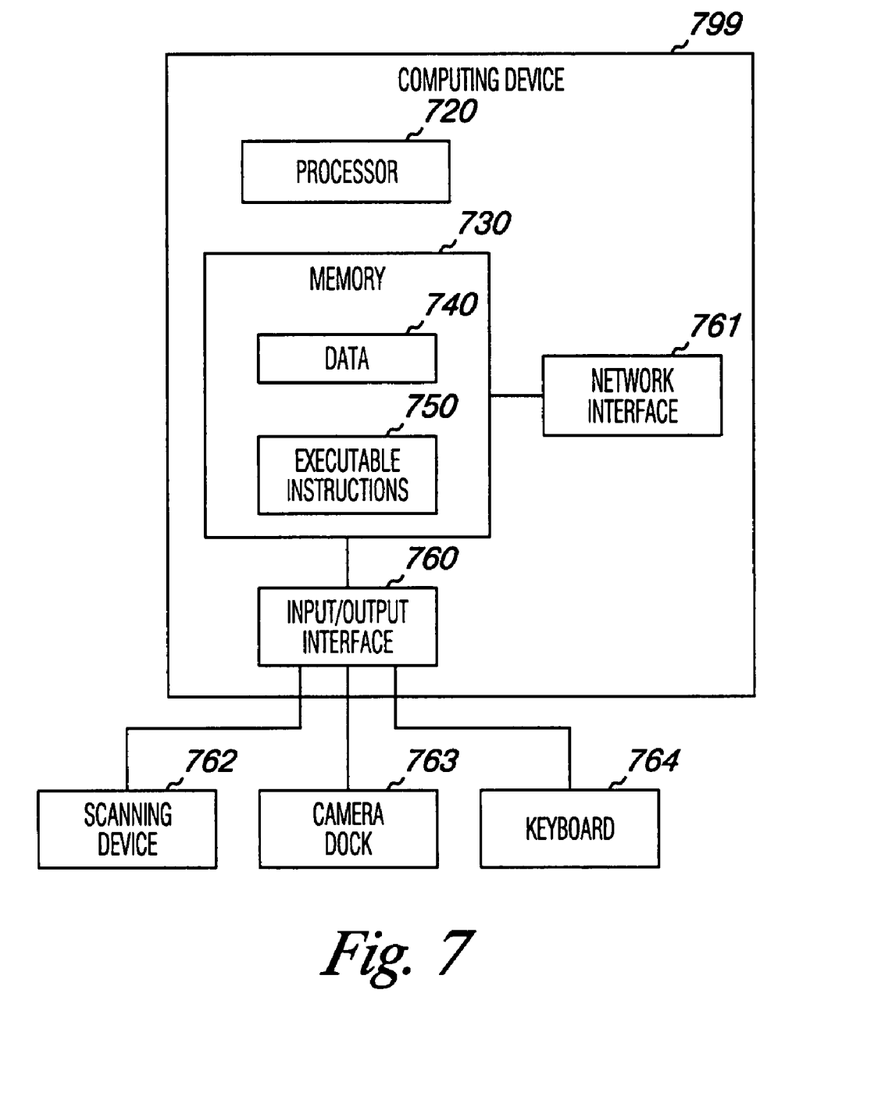
FIG. 7 provides a system for analyzing various physical teeth and associating an abnormal tooth shape with a model tooth shape and mapping predefined dental references from the model shape onto the abnormal tooth according to embodiments of the present disclosure.

FIG. 7 provides a system for analyzing the positions of various physical teeth and in creating virtual models thereof that can be used with embodiments of the present disclosure. In the system illustrated in FIG. 7, the system includes a computing device 799 having a processor 720 and memory 730. The memory can include various types of information including data 740 and executable instructions 750 as discussed herein.

Additionally, as illustrated in the embodiment of FIG. 7, a system can include a network interface 761. Such an interface can allow for processing on another networked computing device or such devices can be used to obtain information about the patient or executable instructions for use with various embodiments provided herein.

As illustrated in the embodiment of FIG. 7, a system can include one or more input and/or output interfaces 760. Such interfaces can be used to connect the computing device with one or more input or output devices. For example, in the embodiment illustrated in FIG. 7, the system includes connectivity to a scanning device 762, a camera dock 763, and a keyboard 764.

Such connectivity can allow for the input and/or output of image information (e.g., scanned images or digital pictures, etc.) or instructions (e.g., input via keyboard) among other types of information. Although some embodiments may be distributed among various computing devices within one or more networks, such systems as illustrated in FIG. 7 can be beneficial in allowing for the capture, calculation, and analysis of the various information discussed herein.

As discussed above, embodiments of the present disclosure also include a number of method embodiments. For example, in some embodiments, a method can include creating a reference library including a set of model tooth shapes with model tooth geometries, where each model tooth shape has a predefined dental reference.

Some embodiments include associating an abnormal tooth shape with a model tooth shape from the reference library. This can be beneficial in aiding the treatment professional with visualization of references for an abnormal tooth.

As discussed above, such embodiments can include references which might not be visible on an abnormal tooth due to its abnormality. For example, a chipped tooth could be missing a portion of the tooth where a dental reference is located.

Embodiments can include superimposing the model tooth shape on the abnormal tooth shape. This can be beneficial in allowing the treatment professional to visualize the shape and references from a model tooth shape superimposed on the abnormal tooth shape representing a tooth possibly requiring treatment.

Various embodiments can include mapping the predefined dental reference from the model tooth shape onto at least a portion of the abnormal tooth shape. This can be beneficial in providing the treatment professional with more accurate and consistent references over manual selection of references based on the treatment professional's estimation.

Some embodiments include adding a location of the predefined dental reference to the abnormal tooth shape based on the mapped predefined dental reference from the model tooth shape. This can aid the treatment professional when correction of the abnormal tooth involves treatment in consideration of that reference point.

Embodiments can include superimposing the model tooth shape on the abnormal tooth shape by a best-fit algorithm. This can be beneficial in further automating the process of matching reference points from a model tooth shape with an abnormal tooth shape.

In some embodiments, for example, each model tooth shape can have at least six predefined dental references. The one or more reference points can be individual points, lines, shapes, or other markers that can be used to determine an object's position in space. This can be beneficial in allowing a treatment professional to have enough information to accurately characterize a tooth's movement.

In some embodiments, the predefined dental references can include virtual orthodontic brackets (e.g., 370-13 in FIG. 3A). Virtual orthodontic brackets on a plurality of teeth in a jaw, for example, can be lined up using a virtual wire.

In so doing, a prescription can be built into the virtual bracket for inclination, angulation, rotation, and/or in-out, for example, based on the modeled teeth templates. The modeled teeth templates can be custom adjusted to fit the actual teeth using a best fit algorithm, such as that described above.

As discussed with respect to FIG. 7, embodiments of the present disclosure also include a computing device including a processor, memory connected to the processor, and computing device executable instructions storable in the memory and executable by the processor. For example, in some embodiments, the device can associate an abnormal tooth shape with a model tooth shape from a reference library of model tooth shapes, map a predefined dental reference from the model tooth shape onto at least a portion of the abnormal tooth shape, and add a location of the predefined dental references to the abnormal tooth based on the mapped predefined dental references from the model tooth.

Such functions can be provided by executable instructions stored in memory and executable by a logic circuit such as a processor. The library files and/or related tooth shape information can also be stored in memory.

In some embodiments, the memory of the computing device includes the reference library including a set of model tooth shapes with model tooth geometries, where each model tooth shape includes the predefined dental references. The model tooth shapes and predefined dental references can be utilized by the device to allow a treatment professional to accurately characterize a tooth's movement as discussed above.

In some embodiments, the computing device can include executable instructions to create a dental image of the abnormal tooth shape, where abnormalities of the abnormal tooth shape are virtually corrected by the superimposed model tooth shape. This can be beneficial in allowing the treatment professional to accurately characterize a tooth's movement based on accurate and correct dental references as discussed above.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A non-transitory computing device readable medium having executable instructions which can be executed by a processor to cause a computing device to perform a method, comprising:

associating an abnormal tooth shape representing an abnormal tooth or a not fully erupted tooth of a patient with a model tooth shape representing a normal fully erupted tooth from a reference library of model tooth shapes representing normal fully erupted teeth;

mapping a predefined dental reference identified from information comprising the model tooth shape onto at least an abnormal portion of the abnormal tooth shape in a position that the predefined dental reference would assume if the abnormal tooth shape were a normal tooth shape; and adding a location of the predefined dental reference to the abnormal tooth shape based on the mapped predefined dental reference from the model tooth shape.

2. The medium of claim 1, where mapping the predefined dental reference from the model tooth onto at least the abnormal portion of the abnormal tooth includes superimposing the model tooth shape on the abnormal tooth shape.

3. The medium of claim 1, where the method includes creating a dental image that contains at least a portion of the abnormal tooth shape and at least a portion of the model tooth shape.

4. The medium of claim 3, where the method includes mapping a predefined gingival reference from the reference library corresponding to the model tooth shape onto a gingival anatomy of the abnormal tooth shape, where the dental image contains at least a portion of the abnormal tooth shape gingival anatomy and at least a portion of the model tooth shape gingival anatomy.

5. The medium of claim 1, where mapping the predefined dental reference from the model tooth shape onto at least the abnormal portion of the abnormal tooth shape includes virtually mapping a portion of the predefined dental reference that does not correspond to a location on the abnormal tooth shape.

6. The medium of claim 1, where the method includes determining a center of rotation of the abnormal tooth shape using the location of the predefined dental references on the abnormal tooth shape based on the mapped predefined dental references from the model tooth shape.

7. The medium of claim 1, where the method includes creating an orthodontic treatment plan based on the location of the predefined dental references on the abnormal tooth shape.

8. The medium of claim 7, where creating an orthodontic treatment plan includes creating a predefined set of appliances for placement over one or more teeth.

9. A method of determining dental references, comprising:
predefining a dental reference from information comprising each model tooth shape in a reference library including a set of model tooth shapes with model tooth geometries representing normal fully erupted teeth;
associating an abnormal tooth shape representing an abnormal tooth or not fully erupted tooth of a patient with a model tooth shape representing a normal fully erupted tooth from the reference library;
superimposing the model tooth shape on the abnormal tooth shape;
mapping the predefined dental reference from the model tooth shape onto at least an abnormal portion of the abnormal tooth shape in a position that the predefined dental reference would assume if the abnormal tooth shape were a normal tooth shape; and
adding a location of the predefined dental reference to the abnormal tooth shape based on the mapped predefined dental reference from the model tooth shape.

10. The method of claim 9, where superimposing the model tooth shape on the abnormal tooth shape is performed by a best-fit algorithm.

11. The method of claim 9, where each model tooth shape has at least six predefined dental references.

12. The method of claim 9, where the predefined dental references can include virtual orthodontic brackets.

13. The method of claim 9, where mapping the predefined dental reference from the model tooth shape onto at least the abnormal portion of the abnormal tooth shape includes virtually mapping a portion of the predefined dental reference that does not correspond to a location on the abnormal tooth shape.

14. The method of claim 9, where superimposing the model tooth shape on the abnormal tooth shape includes creating a dental image that contains at least a portion of the abnormal tooth shape and at least a portion of the model tooth shape.

15. A computing device, comprising:
a processor;
a memory connected to the processor; and
computing device executable instructions storable in the memory and executable by the processor to:
associate an abnormal tooth shape representing an abnormal tooth or a not fully erupted tooth of a patient with a model tooth shape representing a normal fully erupted tooth from a reference library of model tooth shapes representing normal fully erupted teeth;
map a predefined dental reference identified from information comprising the model tooth shape onto at least an abnormal portion of the abnormal tooth shape in a position that the predefined dental reference would assume if the abnormal tooth shape were a normal tooth shape; and
add a location of the predefined dental references to the abnormal tooth based on the mapped predefined dental references from the model tooth.

16. The computing device of claim 15, where the memory includes the reference library including a set of model tooth shapes with model tooth geometries, where each model tooth shape includes the predefined dental references.

17. The computing device of claim 15, where the device includes computing device executable instructions to superimpose the model tooth shape on the abnormal tooth shape.

18. The computing device of claim 17, where the device includes computing device executable instructions to create a dental image of the abnormal tooth shape, where abnormalities of the abnormal tooth shape are virtually corrected by the superimposed model tooth shape.

19. The computing device of claim 17, where superimposing the model tooth shape on the abnormal tooth shape is performed by a shrink-wrap sizing algorithm.

20. The computing device of claim 15, where mapping the predefined dental reference from the model tooth shape onto at least the abnormal portion of the abnormal tooth shape includes virtually mapping a portion of the predefined dental reference that does not correspond to a location on the abnormal tooth shape.

21. The computing device of claim 15, where the device includes computing device executable instructions to virtually map a portion of the predefined dental reference that is at least partially obscured by the gingiva.

* * * * *